(12) United States Patent
Weisman et al.

(10) Patent No.: US 9,597,207 B2
(45) Date of Patent: *Mar. 21, 2017

(54) DELIVERY SYSTEM HAVING STENT LOCKING STRUCTURE

(71) Applicant: Boston Scientific Scimed, Inc., Maple Grove, MN (US)

(72) Inventors: Michal Weisman, Winchester, MA (US); Michael D. Amos, Ayer, MA (US); Andrew K. Hollett, Somerville, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 277 days.

This patent is subject to a terminal disclaimer.

(21) Appl. No.: 14/269,719

(22) Filed: May 5, 2014

(65) Prior Publication Data

US 2014/0243948 A1    Aug. 28, 2014

Related U.S. Application Data

(63) Continuation of application No. 12/884,997, filed on Sep. 17, 2010, now Pat. No. 8,753,303.
(Continued)

(51) Int. Cl.
*A61F 2/00* (2006.01)
*A61F 2/848* (2013.01)
(Continued)

(52) U.S. Cl.
CPC ............... *A61F 2/848* (2013.01); *A61F 2/95* (2013.01); *A61F 2/94* (2013.01); *A61F 2/966* (2013.01);
(Continued)

(58) Field of Classification Search
CPC .... A61F 2/848; A61F 2/94; A61F 2/95; A61F 2/966; A61F 2002/041;
(Continued)

(56) References Cited

U.S. PATENT DOCUMENTS 2,212,334 A    8/1940 Wallerich
2,393,003 A    1/1946 Smith
(Continued)

FOREIGN PATENT DOCUMENTS

CA    1112119 A    11/1981
DE    3345612 A1    6/1985
(Continued)

*Primary Examiner* — Jacqueline Stephens
*Assistant Examiner* — Benjamin Klein
(74) *Attorney, Agent, or Firm* — Seager, Tufte & Wickhem, LLP

(57) ABSTRACT

A drainage stent delivery system including an elongate shaft of a medial device, a drainage catheter or stent, and a locking mechanism for selectively coupling the drainage stent to the elongate shaft. The drainage stent is selectively coupled to a distal portion of the elongate shaft such that the proximal end of the stent is positioned proximal of the distal end of the elongate shaft. The locking mechanism includes an engaging feature of the elongate shaft which engages a portion of the stent such that the stent may be selectively coupled to the elongate shaft through rotational motion of the elongate shaft relative to the stent. In some instances, the engaging feature of the elongate shaft may be a tab which extends into an opening of the stent.

20 Claims, 16 Drawing Sheets

Related U.S. Application Data

(60) Provisional application No. 61/245,861, filed on Sep. 25, 2009.

(51) Int. Cl.
  *A61F 2/95*    (2013.01)
  *A61F 2/94*    (2013.01)
  *A61F 2/966*   (2013.01)
  *A61F 2/04*    (2013.01)

(52) U.S. Cl.
  CPC . *A61F 2002/041* (2013.01); *A61F 2002/8483* (2013.01); *A61F 2002/9505* (2013.01)

(58) Field of Classification Search
  CPC ...... A61F 2002/8483; A61F 2002/9505; A61F 9/00781
  See application file for complete search history.

(56) References Cited

U.S. PATENT DOCUMENTS

| | | |
|---|---|---|
| 3,100,490 A | 8/1963 | Desautels |
| 3,332,424 A | 7/1967 | Minteer |
| 3,421,509 A | 1/1969 | Fiore |
| 3,592,197 A | 7/1971 | Cohen |
| 3,783,453 A | 1/1974 | Bolie |
| 3,908,635 A | 9/1975 | Viek |
| 3,938,529 A | 2/1976 | Gibbons |
| 3,995,642 A | 12/1976 | Adair |
| 4,212,304 A | 7/1980 | Finney |
| 4,225,979 A | 10/1980 | Rey et al. |
| 4,242,304 A | 12/1980 | Ryder |
| 4,248,214 A | 2/1981 | Hannah et al. |
| 4,307,723 A | 12/1981 | Finney |
| 4,334,327 A | 6/1982 | Lyman et al. |
| 4,382,445 A | 5/1983 | Sommers |
| 4,434,797 A | 3/1984 | Silander |
| 4,474,569 A | 10/1984 | Newkirk |
| 4,484,585 A | 11/1984 | Baier |
| 4,500,313 A | 2/1985 | Young |
| 4,531,933 A | 7/1985 | Norton et al. |
| 4,545,373 A | 10/1985 | Christoudias |
| 4,568,338 A | 2/1986 | Todd |
| 4,592,341 A | 6/1986 | Omagari et al. |
| 4,610,657 A | 9/1986 | Densow |
| 4,643,716 A | 2/1987 | Drach |
| 4,645,493 A | 2/1987 | Ferrando et al. |
| 4,671,795 A | 6/1987 | Mulchin |
| 4,684,369 A | 8/1987 | Wildemeersch |
| 4,699,611 A | 10/1987 | Bowden |
| 4,713,049 A | 12/1987 | Carter |
| 4,738,667 A | 4/1988 | Galloway |
| 4,747,833 A | 5/1988 | Kousai et al. |
| 4,755,175 A | 7/1988 | Nilsson |
| 4,762,128 A | 8/1988 | Rosenbluth |
| 4,783,454 A | 11/1988 | Liu |
| 4,784,651 A | 11/1988 | Hickey |
| 4,787,884 A | 11/1988 | Goldberg |
| 4,790,809 A | 12/1988 | Kuntz |
| 4,790,810 A | 12/1988 | Pugh, Jr. et al. |
| 4,813,925 A | 3/1989 | Anderson, Jr. et al. |
| 4,820,262 A | 4/1989 | Finney |
| 4,822,333 A | 4/1989 | Lavarenne |
| 4,824,435 A | 4/1989 | Giesy et al. |
| 4,832,055 A | 5/1989 | Palestrant |
| 4,874,360 A | 10/1989 | Goldberg et al. |
| 4,886,065 A | 12/1989 | Collins, Jr. |
| 4,913,141 A | 4/1990 | Hillstead |
| 4,913,683 A | 4/1990 | Gregory |
| 4,931,037 A | 6/1990 | Wetterman |
| 4,950,228 A | 8/1990 | Knapp, Jr. et al. |
| 4,955,858 A | 9/1990 | Drews |
| 4,957,479 A | 9/1990 | Roemer |
| 4,963,129 A | 10/1990 | Rusch |
| 4,973,301 A | 11/1990 | Nissenkorn |
| 4,990,133 A | 2/1991 | Solazzo |
| 4,994,066 A | 2/1991 | Voss |
| 5,019,085 A | 5/1991 | Hillstead |
| 5,019,102 A | 5/1991 | Hoene |
| 5,052,998 A | 10/1991 | Zimmon |
| 5,098,374 A | 3/1992 | Othel-Jacobsen et al. |
| 5,116,309 A | 5/1992 | Coll |
| 5,141,502 A | 8/1992 | Macaluso, Jr. |
| 5,147,370 A | 9/1992 | McNamara et al. |
| 5,152,749 A | 10/1992 | Giesy et al. |
| 5,160,341 A | 11/1992 | Brenneman et al. |
| 5,234,437 A | 8/1993 | Sepetka |
| 5,250,071 A | 10/1993 | Palermo |
| 5,261,916 A | 11/1993 | Engelson |
| 5,267,958 A | 12/1993 | Buchbinder et al. |
| 5,282,784 A | 2/1994 | Willard |
| 5,295,954 A | 3/1994 | Sachse |
| 5,304,195 A | 4/1994 | Twyford, Jr. et al. |
| 5,304,198 A | 4/1994 | Samson |
| 5,320,604 A | 6/1994 | Walker et al. |
| 5,322,501 A | 6/1994 | Mahmud-Durrani |
| 5,324,259 A | 6/1994 | Taylor et al. |
| 5,334,185 A | 8/1994 | Giesy et al. |
| 5,346,467 A | 9/1994 | Coll |
| 5,348,537 A | 9/1994 | Wiesner et al. |
| 5,354,263 A | 10/1994 | Coll |
| 5,364,340 A | 11/1994 | Coll |
| 5,364,354 A | 11/1994 | Walker et al. |
| 5,364,376 A | 11/1994 | Horzewski et al. |
| 5,372,600 A | 12/1994 | Beyar et al. |
| 5,391,155 A | 2/1995 | Sachse |
| 5,399,165 A | 3/1995 | Paul, Jr. |
| 5,401,257 A | 3/1995 | Chevalier, Jr. et al. |
| 5,405,378 A | 4/1995 | Strecker |
| 5,407,435 A | 4/1995 | Sachse |
| 5,409,468 A | 4/1995 | Sachse |
| 5,454,788 A | 10/1995 | Walker et al. |
| 5,458,615 A | 10/1995 | Klemm et al. |
| 5,476,505 A | 12/1995 | Limon |
| 5,480,434 A | 1/1996 | Eckstein et al. |
| 5,484,409 A | 1/1996 | Atkinson et al. |
| 5,496,344 A | 3/1996 | Kanesaka et al. |
| 5,540,236 A | 7/1996 | Ginn |
| 5,578,009 A | 11/1996 | Kraus et al. |
| 5,599,291 A | 2/1997 | Balbierz et al. |
| 5,639,274 A | 6/1997 | Fischell et al. |
| 5,645,533 A | 7/1997 | Blaeser et al. |
| 5,653,748 A | 8/1997 | Strecker |
| 5,669,880 A | 9/1997 | Solar |
| 5,676,654 A | 10/1997 | Ellis et al. |
| 5,681,274 A | 10/1997 | Perkins et al. |
| 5,690,642 A | 11/1997 | Osborne et al. |
| 5,693,015 A | 12/1997 | Walker et al. |
| 5,776,099 A | 7/1998 | Tremulis |
| 5,921,952 A | 7/1999 | Desmond, III et al. |
| 5,921,971 A | 7/1999 | Agro et al. |
| 6,095,990 A | 8/2000 | Parodi |
| 6,159,177 A | 12/2000 | Amos, Jr. et al. |
| 6,159,195 A | 12/2000 | Ha et al. |
| 6,248,100 B1 | 6/2001 | de Toledo et al. |
| 6,264,624 B1 | 7/2001 | Desmond, III et al. |
| 6,451,025 B1 | 9/2002 | Jervis |
| 6,562,024 B2 | 5/2003 | Alvarez de Toledo et al. |
| 6,776,791 B1 * | 8/2004 | Stallings ............... A61F 2/07 623/1.11 |
| 7,087,038 B2 | 8/2006 | Lee |
| 7,326,224 B2 | 2/2008 | Houde et al. |
| 7,550,002 B2 | 6/2009 | Goto et al. |
| 8,753,303 B2 * | 6/2014 | Weisman ............... A61F 2/95 604/8 |
| 2005/0085891 A1 * | 4/2005 | Goto ............... A61F 2/94 623/1.11 |
| 2005/0085892 A1 * | 4/2005 | Goto ............... A61F 2/94 623/1.12 |
| 2006/0212009 A1 | 9/2006 | Accisano, III et al. |
| 2007/0186933 A1 | 8/2007 | Domingo et al. |
| 2007/0293929 A1 | 12/2007 | Aoba et al. |
| 2009/0143849 A1 | 6/2009 | Ozawa et al. |
| 2009/0312829 A1 | 12/2009 | Aoba et al. |

(56) References Cited

U.S. PATENT DOCUMENTS

FOREIGN PATENT DOCUMENTS

| DE | 3919740 A1 | 12/1990 |
|----|------------|---------|
| EP | 1792575    | 6/2007  |
| GB | 2018600 A  | 10/1979 |
| WO | 9300126 A1 | 1/1993  |
| WO | 9908740    | 2/1999  |
| WO | 2007053568 | 5/2007  |

* cited by examiner

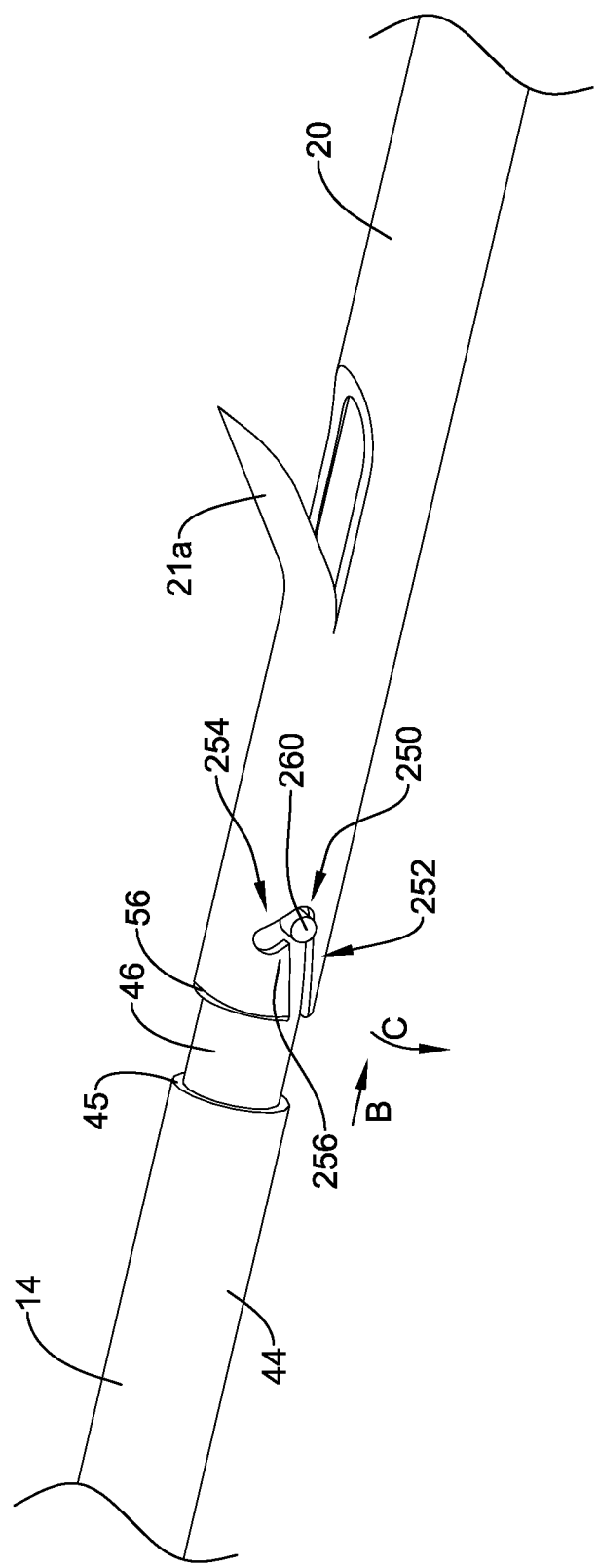

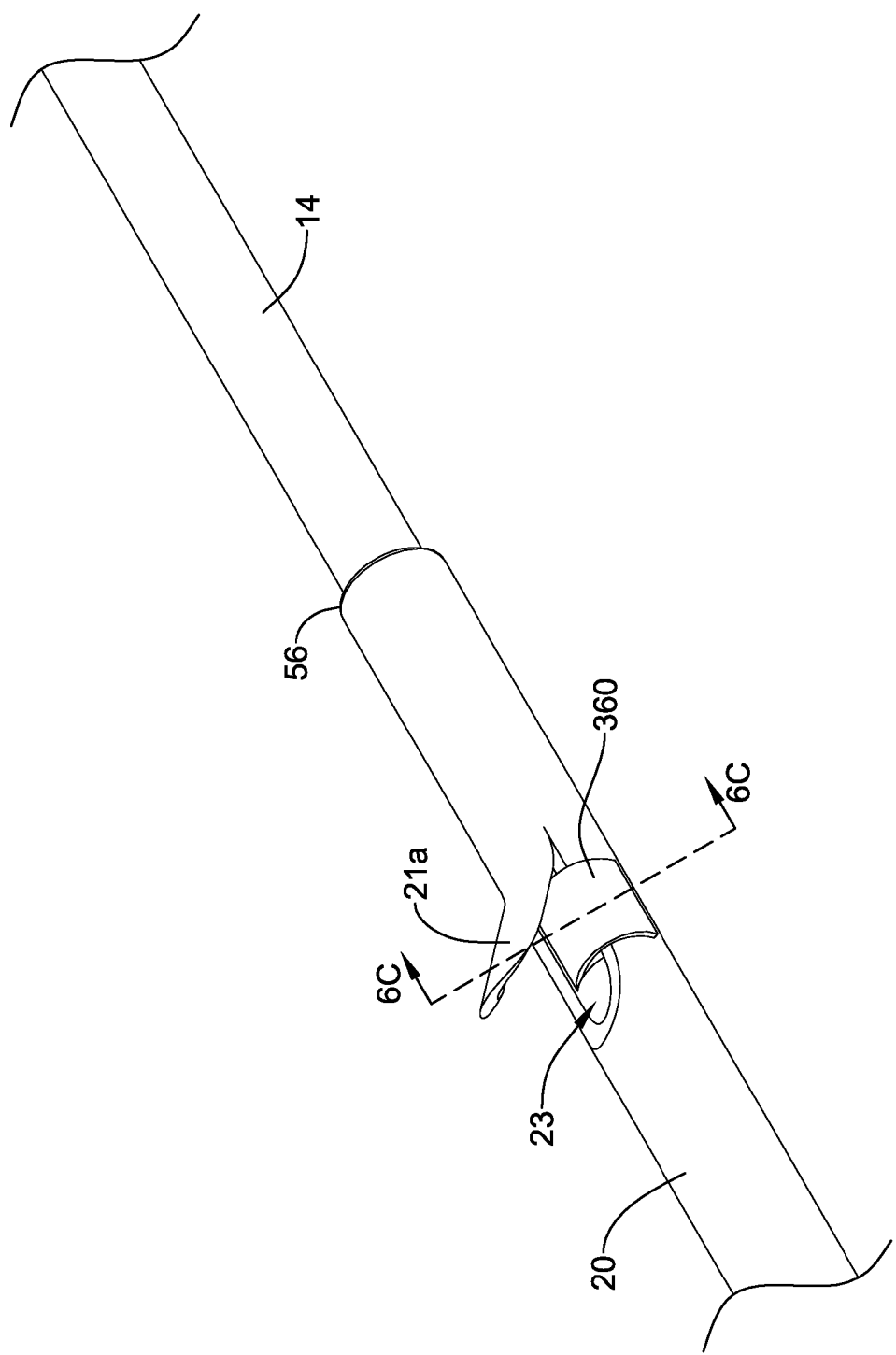

DELIVERY SYSTEM HAVING STENT LOCKING STRUCTURE

CROSS REFERENCE TO RELATED APPLICATIONS

This application is a continuation of U.S. application Ser. No. 12/884,997, filed Sep. 17, 2010, which claims the benefit of U.S. Provisional Application Ser. No. 61/245,861, filed Sep. 25, 2009, the disclosures of which are incorporated herein by reference.

TECHNICAL FIELD

The disclosure is directed to a locking structure of a medical device. More particularly, the disclosure is directed to a stent locking structure for selectively locking a stent to a shaft of a stent delivery system. Specifically, the disclosure is directed to a locking structure for selectively locking a drainage stent to a catheter shaft of a drainage stent delivery system.

BACKGROUND

Medical devices, such as catheters, are widely used in various medical procedures to access remote anatomical locations and/or deploy therapeutic devices. One exemplary catheter system is a drainage stent delivery system configured to deliver a drainage stent (e.g., a drainage catheter) to a body lumen, such as a lumen of the biliary tree or a ureter. It may be desirable to releasably connect the drainage stent to the delivery system in order to provide the medical personnel with control over positioning and deployment of the drainage catheter in a body lumen without premature deployment of the drainage stent from the delivery system. Some exemplary drainage stent delivery systems including features for releasably connecting a drainage stent to a delivery system are disclosed in U.S. Pat. Nos. 5,921,952 and 6,562,024, the disclosures of which are incorporated herein by reference. For instance, a releasable connecting feature in the form of a flexible thread or suture may be used for releasably connecting the drainage stent to a shaft of the drainage stent delivery system.

However, a need remains to provide alternative embodiments of a locking system to releasably lock a stent, such as a vascular stent or a drainage stent, or other endoprosthesis to a stent delivery system, such as a vascular stent or drainage stent delivery system, which allows controlled positioning and deployment of the stent in a body lumen.

SUMMARY

The disclosure is directed to several alternative designs and configurations of medical device structures and assemblies including a locking structure for selectively locking a stent to a delivery system.

Accordingly, one illustrative embodiment is a stent delivery system including an elongate shaft of a medial device, a stent, and a locking mechanism for selectively coupling the stent to the elongate shaft. The stent may be selectively coupled to a distal portion of the elongate shaft such that the proximal end of the stent is positioned proximal of the distal end of the elongate shaft. The locking mechanism includes an engaging feature of the elongate shaft which engages a portion of the stent such that the stent may be selectively coupled to the elongate shaft through rotational motion of the elongate shaft relative to the stent. In some instances the engaging feature of the elongate shaft may be a tab which extends into an opening of the stent.

Another illustrative embodiment is a drainage stent delivery system including a drainage stent including a tubular member having a proximal end and a distal end, and an elongate shaft extending distally from a handle assembly to a location distal of the proximal end of the drainage stent. A distal portion of the elongate shaft includes a tab which is configured for engagement with the drainage stent through rotational motion of the elongate shaft relative to the drainage stent to selectively couple the drainage stent to the elongate shaft. In some instances the tab may be a radially extending protrusion or a circumferentially extending arcuate flap.

Another illustrative embodiment is a stent delivery system including an elongate shaft of a medical device and a stent. The stent is selectively coupled to a distal portion of the elongate shaft such that the proximal end of the stent is positioned proximal of the distal end of the elongate shaft. The stent delivery system also includes means for selectively coupling the stent to the elongate shaft through rotational motion of the elongate shaft relative to the stent.

Yet another illustrative embodiment is a method of selectively engaging a stent to an elongate shaft of a medical device. The method includes positioning a stent relative to an elongate shaft of a medical device such that a distal end of the elongate shaft is distal of a proximal end of the stent. The stent is rotated relative to the elongate shaft such that a tab of the elongate shaft extends into an opening of the stent. In some instances, after rotating the stent relative to the elongate shaft, an outer tubular member of the elongate shaft is actuated distally relative to an inner tubular member of the elongate shaft to abut the proximal end of the stent.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIGS. 5A-5D are perspective views illustrating the functionality of another locking structure for selectively coupling a stent to an elongate shaft of a delivery system;

FIGS. 6A and 6B are perspective views illustrating the functionality of another locking structure for selectively coupling a stent to an elongate shaft of a delivery system;

Figure 1:
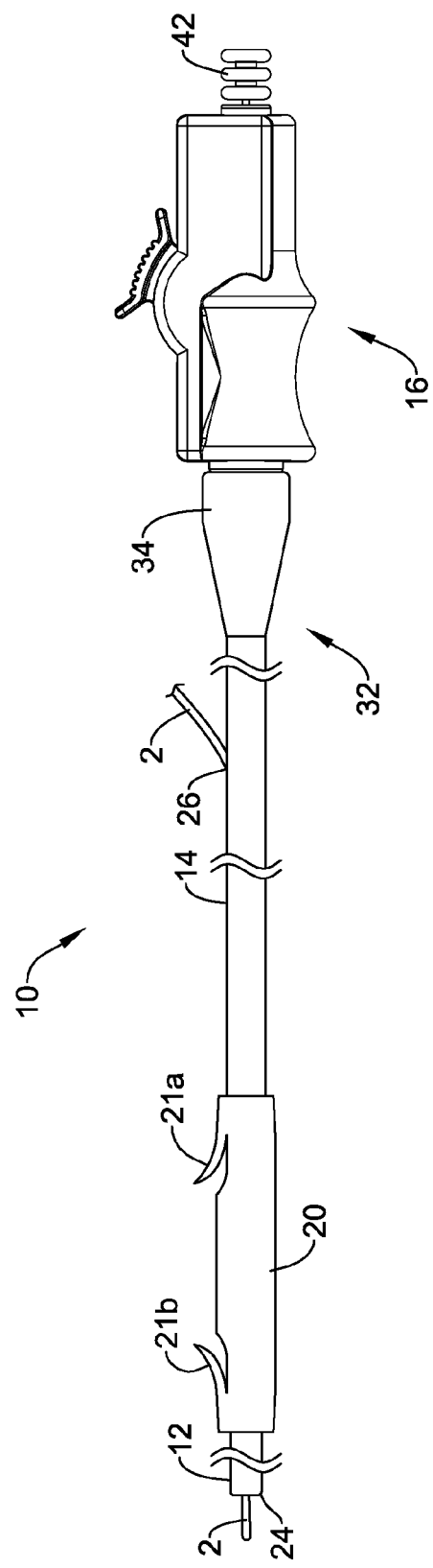
FIG. 1 is a plan view of an exemplary drainage stent delivery system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the term "proximal" refers to a direction that is generally toward a physician during a medical procedure, while the term "distal" refers to a direction that is generally toward a target site within a patient's anatomy during a medical procedure.

As used in this specification and the appended claims, the term "body lumen" means any body passage cavity that conducts fluid, including but not limited to biliary ducts, pancreatic ducts, ureteral passages, esophagus, and blood vessels such as those of the human vasculature system.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
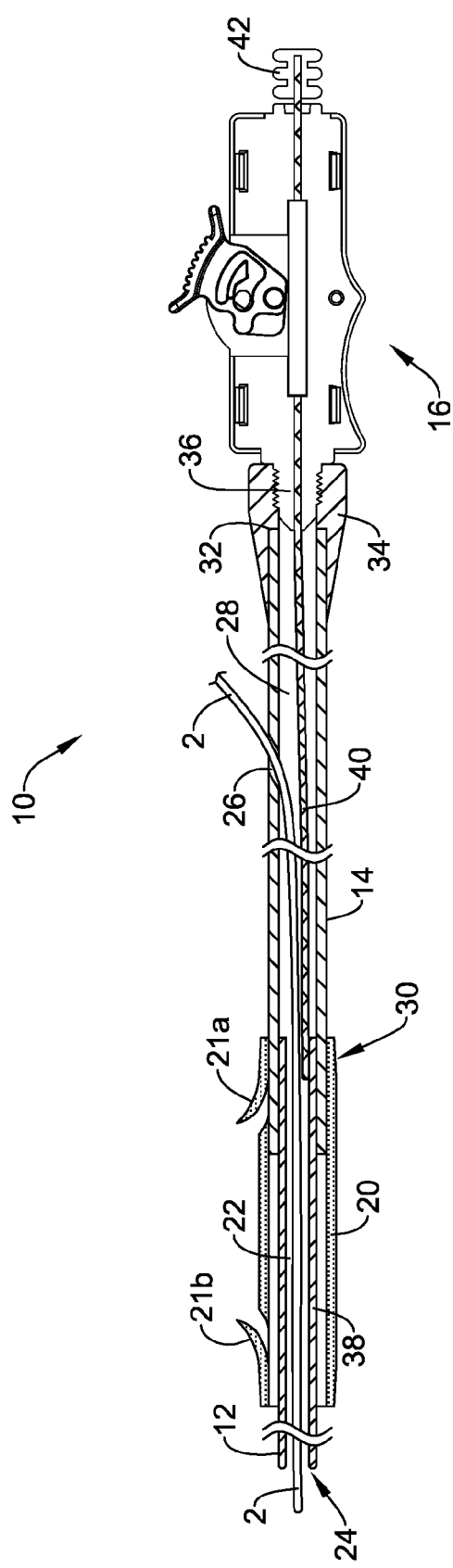
FIG. 2 is a longitudinal cross-sectional view of the drainage stent delivery system of FIG. 1.

Referring now to FIGS. 1 and 2, there is shown an exemplary medical device, illustrated as a drainage stent delivery system 10 for delivering a drainage catheter or stent 20 to an anatomical location, such as in a lumen of the biliary tree or a ureter. The drainage stent 20 may be used to bypass or drain an obstructed lumen and can be configured for long-term positioning within the lumen. In some embodiments, the drainage stent 20 may include one or more, or a plurality of barbs 21, or other retention features that may help prevent migration of the drainage stent 20 when positioned in a body lumen. The illustrated drainage stent 20 includes a proximal barb 21a and a distal barb 21b. It should be understood that the terms "drainage catheter" and "drainage stent" can be used interchangeably with reference to these applications.

The drainage stent delivery system 10 is designed for use with a conventional guidewire 2 and may include a drainage stent 20, a guide catheter 12, a push catheter 14, and a handle assembly 16. The guidewire 2 may extend into a lumen 22 of the guide catheter 12 through a distal guidewire port 24 and out a proximal guidewire port 26 in a sidewall of the push catheter 14, providing the drainage stent delivery system 10 with single-operator-exchange (SOE) capabilities.

The guide catheter 12 may be slidably disposed in the lumen 28 of the push catheter 14 and extend distally from the distal end of the push catheter 14. The guide catheter 12 may extend through the drainage stent 20 to a location distal of the drainage stent 20. In some embodiments, a distal portion of the push catheter 14, or a component thereof, may extend into the lumen of the drainage stent 20. In some instances, the proximal end of the drainage stent 20 may abut and/or face a distal end or rim of the push catheter 14, or a component thereof, while a distal portion or component of the push catheter 14 extends into the lumen of the drainage stent 20. In other embodiments, the push catheter 14, or a component thereof, may extend over the drainage stent 20, surrounding a portion of the drainage stent 20.

The drainage stent delivery system 10 may include a means for releasably connecting the drainage stent 20 to an elongate shaft of the drainage stent delivery system 10, such as the guide catheter 12 or the push catheter 14 of the drainage stent delivery system 10. When the drainage stent 20 has been properly placed, the drainage stent 20 may be disconnected from the drainage stent delivery system 10 such that the drainage stent 20 remains in the lumen when the guide catheter 12 and/or the push catheter 14 are withdrawn. Some exemplary locking mechanisms for selectively coupling the drainage stent 20 to an elongate shaft of the drainage stent delivery system 10 are further described herein.

The proximal end 32 of the push catheter 14 may be attached to the handle assembly 16. For example, the proximal end 32 may include a female luer lock connector 34 threadably coupled to a threaded male connector 36 of the handle assembly 16. It is understood, however, that the push catheter 14 may be attached to the handle assembly 16 and extend distally therefrom by other means, such as adhesive bonding, welding, friction fit, interlocking fit, or other suitable means. In some instances, a component of the push catheter 14 may be longitudinally (e.g., slidably and/or rotatably) actuatable relative to another component of the push catheter 14. In such embodiments, the handle assembly 16 may be configured such that the actuatable component of the push catheter 14 may be actuated by medical personnel while the stationary component of the push catheter 14 remains stationary relative to the handle assembly 16.

The guide catheter 12 may include a distal tubular portion 38 and a proximal elongate wire 40, such as a pull wire, coupled to the distal tubular portion 38. The elongate wire 40 may be coupled to the distal tubular portion 38 at a coupling location 30. The elongate wire 40 may extend through the lumen 28 of the push catheter 14 to the handle assembly 16 while the distal tubular portion 38 extends through the drainage stent 20 to a location distal of the drainage stent 20.

In some embodiments, the elongate wire 40 may extend through the handle assembly 16 to a location proximal of the handle assembly 16. The proximal end of the elongate wire 40 may terminate at a knob 42 which may be grasped by an operator to manipulate the guide catheter 12.

As shown in FIG. 2, the elongate wire 40 may share the lumen 28 of the push catheter 14 with the guidewire 2 along a portion of the length of the elongate wire 40. Thus, a portion of the elongate wire 40 may extend proximally from the tubular portion 38 along the side of the guidewire 2 through the lumen 28 of the push catheter 14 up to a location where the guidewire 2 exits the proximal guidewire port 26 of the push catheter 14.

During a medical procedure, the drainage stent delivery system 10 may be advanced to a target location in the anatomy of a patient. For instance, the drainage stent delivery system 10 may be advanced over the guidewire 2 to a target location. In some instances, the drainage stent delivery system 10 may be tracked over the guidewire 2 as the drainage stent delivery system 10 is advanced through a working channel of an endoscope. The guidewire 2 may pass through the lumen 22 of the guide catheter 12 and the lumen 28 of the push catheter 14 and exit through the proximal guidewire port 26 of the push catheter 14.

When the drainage stent 20 has been positioned at the target location in a lumen, the operator may then selectively disengage the drainage stent 20 from the drainage stent delivery system 10 and withdraw the drainage stent delivery system 10, or components thereof, proximally relative to the drainage stent 20 to deploy the drainage stent 20 at the target location. For instance, in some embodiments rotational movement of an elongate shaft of the drainage stent delivery system 10 (e.g., the guide catheter 12 and/or the push catheter 14) relative to the drainage stent 20 may disengage or unlock the drainage stent 20 from the drainage stent delivery system 10. Once the drainage stent 20 is disengaged from the guide catheter 12 and/or the push catheter 14, withdrawing the guide catheter 12 and/or the push catheter 14 proximally may release the drainage stent 20 from the drainage stent delivery system 10 in order to deploy the drainage stent 20 at the target location. Once the drainage stent 20 has been properly deployed at the target location, the drainage stent delivery system 10 may then be withdrawn.

Some exemplary locking structures for selectively coupling the drainage stent 20 to a component, such as an elongate shaft, of the drainage stent delivery system 10 will now be further described.

Figure 3A:
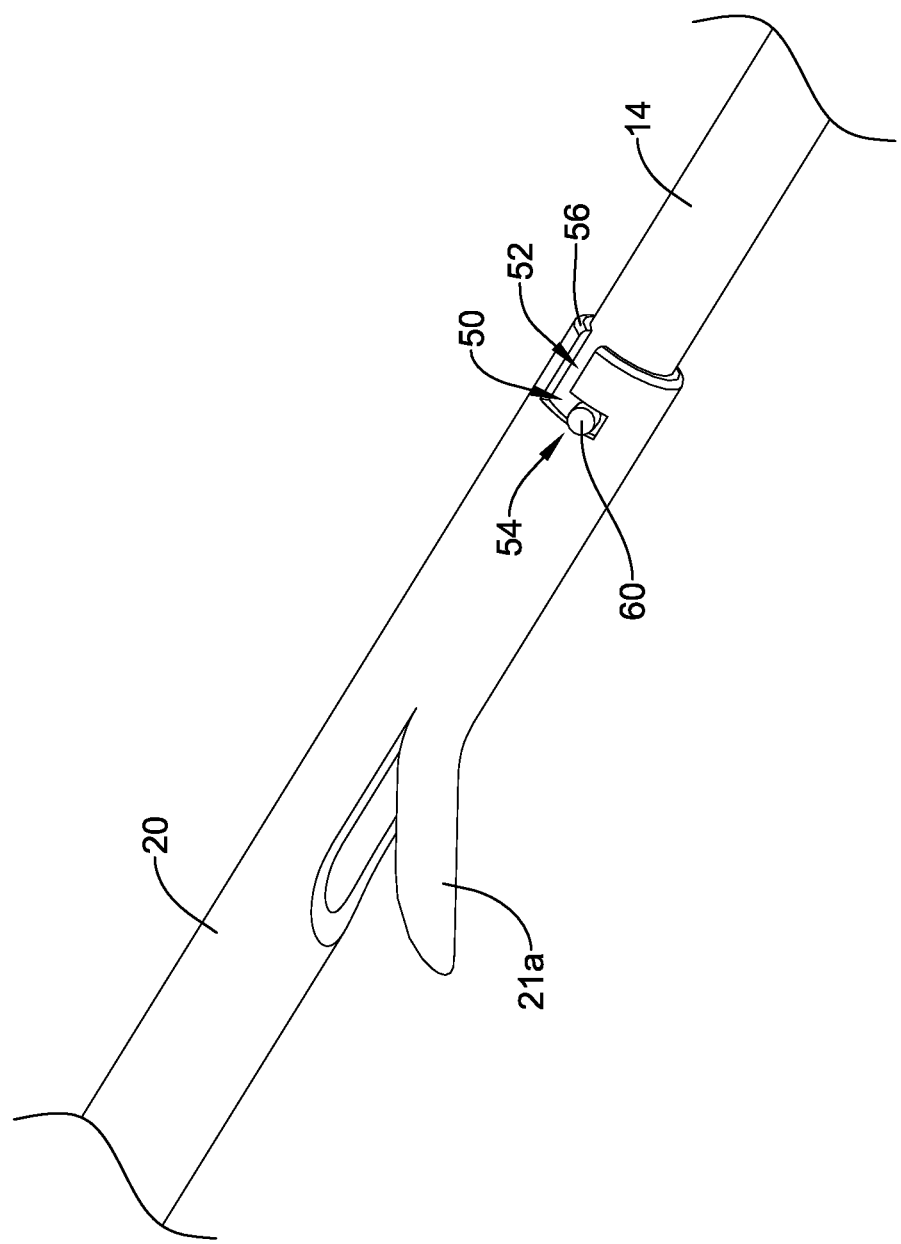
FIGS. 3A and 3B are perspective views illustrating the functionality of an exemplary locking structure for selectively coupling a stent to an elongate shaft of a delivery system.
Figure 3B:
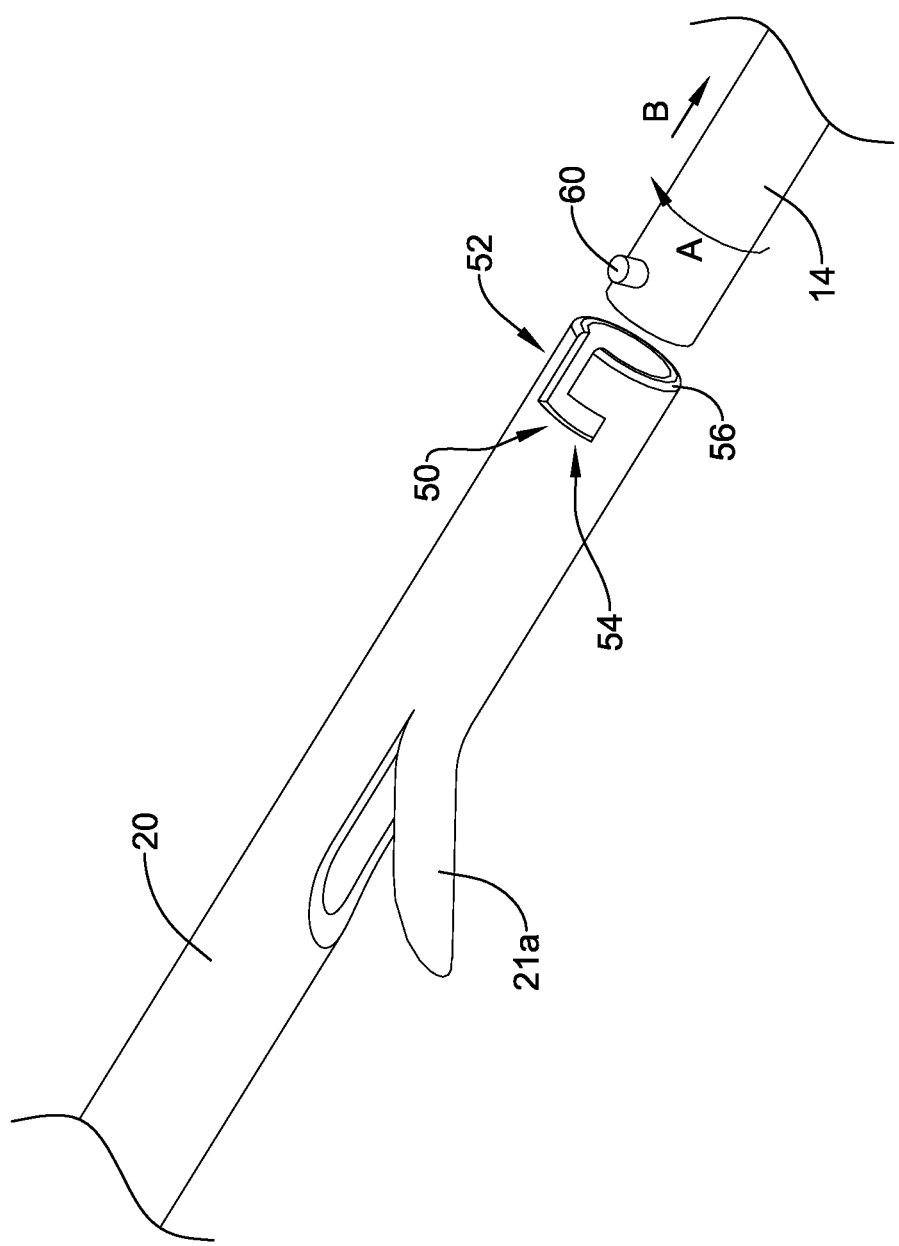

FIGS. 3A and 3B illustrate the functionality of a first exemplary locking structure for selectively coupling the drainage stent 20 to an elongate shaft of the drainage stent delivery system 10. Although the drainage stent 20 is illustrated as being selectively coupled to the push catheter 14 of the drainage stent delivery system 10, it is understood that in some embodiments the drainage stent 20 may be selectively coupled to the guide catheter 12, or another elongate shaft, in the manner described with regard to FIGS. 3A and 3B.

As shown in FIG. 3A, the drainage stent 20 may include an engaging feature which engages with an engaging feature of the push catheter 14 to selectively lock the drainage stent 20 to the push catheter 14. For instance, the push catheter 14 may include a tab 60, such as a radially extending protrusion, extending from the tubular wall of the push catheter 14. The tab 60 may be configured to be inserted into an opening of the drainage stent 20, such as the slot 50. The slot 50 may be formed in or through the tubular wall of the drainage stent 20. As shown in FIGS. 3A and 3B, in some instances, the slot 50 may be an L-shaped slot, opening out to the proximal end 56 of the drainage stent 20. The slot 50 may extend through the entire thickness of the tubular wall of the drainage stent 20, or the slot 50 may only extend through a portion of the thickness of the tubular wall of the drainage stent 20 (e.g., a groove).

The slot 50, shown as an L-shaped slot, may include a first portion 52 extending generally longitudinally from the proximal end 56 of the drainage stent 20 and a second portion 54 extending circumferentially from the first portion 52 in a direction deviating from the first portion 52.

A distal portion of the push catheter 14 may extend into the lumen of the drainage stent 20 such that the tab 60 engages with the slot 50 of the drainage stent 20. Thus, the outer diameter of the distal portion of the push catheter 14 may be less than the inner diameter of the drainage stent 20, while the radial extent of the tab 60 may be greater than the inner diameter of the drainage stent 20. The distal portion of the push catheter 14 may extend into and/or through the lumen of the drainage stent 20 for any desired length such that the proximal end 56 of the drainage stent 20 is positioned proximal of the distal end of the push catheter 14. For instance, with the tab 60 engaged with the slot 50, the distal end of the push catheter 14 may be positioned at or proximal of the proximal barb 21a, between the proximal barb 21a and the distal barb 21b, or at or distal of the distal barb 21b, in some embodiments.

FIG. 3A illustrates the push catheter 14 in a first or engaged position in which the drainage stent 20 is coupled to the push catheter 14. In the engaged position, the tab 60 may be positioned in the second portion 54 of the slot 50 such that longitudinal movement of the push catheter 14 relative to the drainage stent 20 will not decouple the drainage stent 20 from the push catheter 14. For instance, a portion of the tubular wall of the drainage stent 20 may be located proximal of the tab 60 such that if the push catheter 14 is pulled proximally, the tab 60 will contact the tubular wall of the drainage stent 20, preventing disengagement of the drainage stent 20.

As shown in FIG. 3B at arrow A, in order to decouple the drainage stent 20 from the push catheter 14, the push catheter 14 may be rotated relative to the drainage stent 20 to move the tab 60 along the second portion 54 to a location that intersects the first portion 52 of the slot 50. Once the tab 60 is located at the intersection of the first portion 52 and the second portion 54 of the slot 50, the push catheter 14 may be moved longitudinally relative to the drainage stent 20 in a proximal direction, shown by arrow B of FIG. 3B, to a second or disengaged position to withdraw the tab 60 from the slot 50. With the tab 60 decoupled from the slot 50, the push catheter 14 may be withdrawn while the drainage stent 20 is maintained at the target location in a body lumen.

Figure 4A:
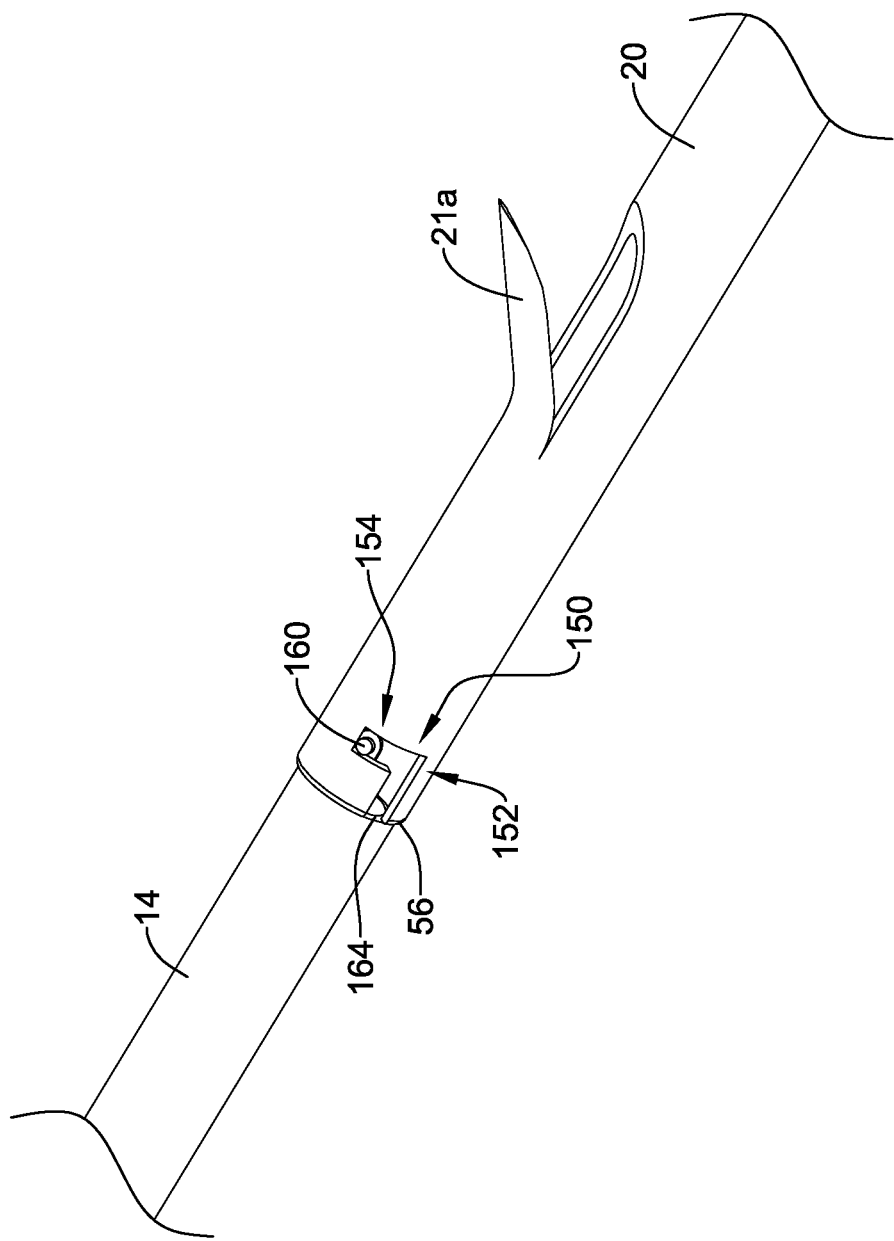
FIGS. 4A and 4B are perspective views illustrating the functionality of another locking structure for selectively coupling a stent to an elongate shaft of a delivery system.
Figure 4B:
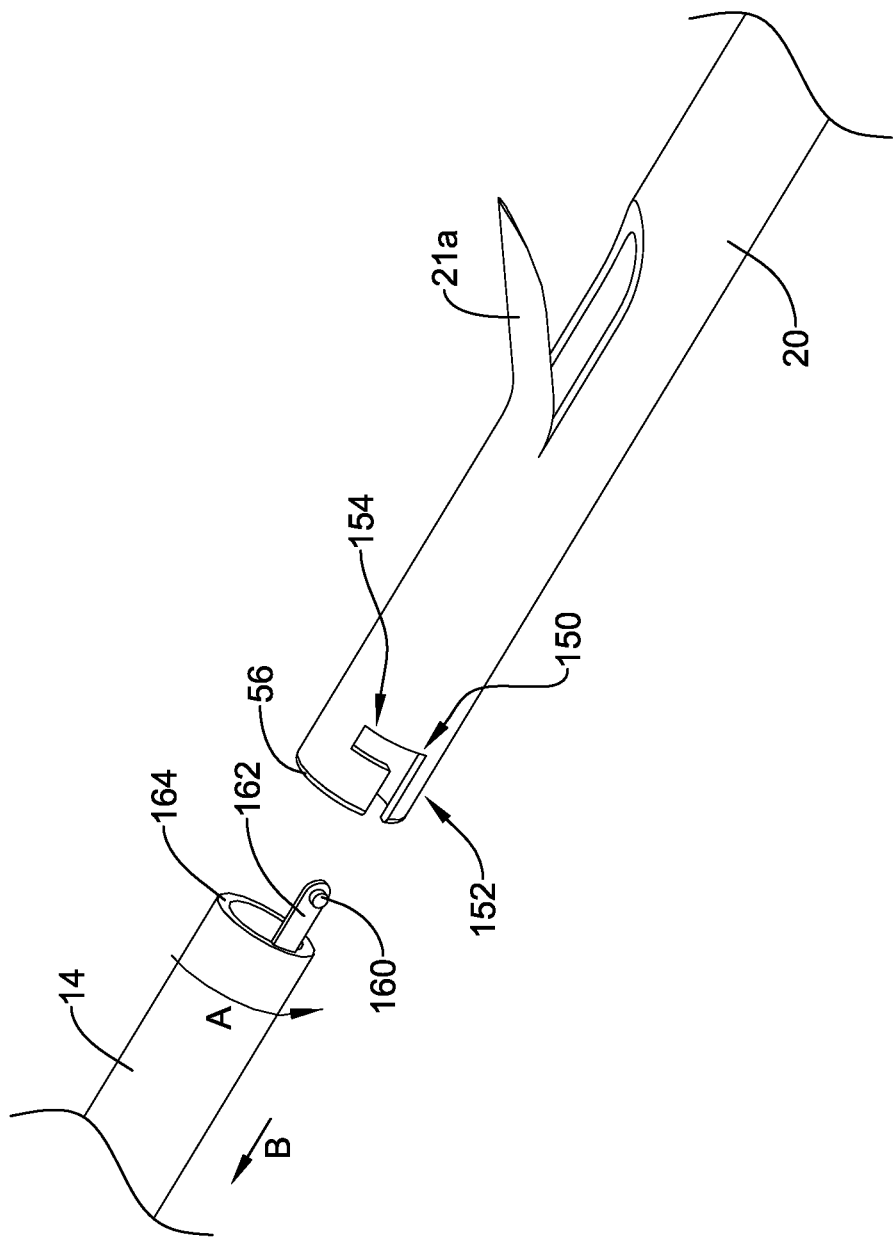

FIGS. 4A and 4B illustrate the functionality of a second exemplary locking structure for selectively coupling the drainage stent 20 to an elongate shaft of the drainage stent delivery system 10. Although the drainage stent 20 is illustrated as being selectively coupled to the push catheter 14 of the drainage stent delivery system 10, it is understood that in some embodiments the drainage stent 20 may be selectively coupled to the guide catheter 12, or another elongate shaft, in the manner described with regard to FIGS. 4A and 4B.

As shown in FIG. 4A, the drainage stent 20 may include an engaging feature which engages with an engaging feature of the push catheter 14 to selectively lock the drainage stent 20 to the push catheter 14. For instance, the push catheter 14 may include an extension 162 extending from a tubular wall, defining an annular distal rim 164, of the push catheter 14 to a distal end of the push catheter 14. The extension 162 may include a tab 160, such as a radially extending protrusion, extending from the extension 162 of the push catheter 14. The tab 160 may be configured to be inserted into an opening of the drainage stent 20, such as the slot 150. The slot 150 may be formed in or through the tubular wall of the drainage stent 20. As shown in FIGS. 4A and 4B, in some instances, the slot 150 may be an L-shaped slot, opening out to the proximal end 56 of the drainage stent 20. The slot 150 may extend through the entire thickness of the tubular wall of the drainage stent 20, or the slot 150 may only extend through a portion of the thickness of the tubular wall of the drainage stent 20 (e.g., a groove).

The slot 150, shown as an L-shaped slot, may include a first portion 152 extending generally longitudinally from the proximal end 56 of the drainage stent 20 and a second portion 154 extending circumferentially from the first portion 152 in a direction deviating from the first portion 152.

The extension 162 of the push catheter 14 may extend into the lumen of the drainage stent 20 such that the tab 160 engages with the slot 150 of the drainage stent 20, while the annular distal rim 164 faces and/or abuts the proximal end 56 of the drainage stent 20. Thus, the outer diameter of the tubular portion of the push catheter 14 may be greater than the inner diameter of the drainage stent 20, whereas the radial extent of the extension 162 from the central longitudinal axis of the push catheter 14 may be less than the inner diameter of the drainage stent 20 and the radial extent of the tab 160 may be greater than the inner diameter of the drainage stent 20. The extension 162 of the push catheter 14 may extend into the lumen of the drainage stent 20 for any desired length such that the proximal end 56 of the drainage stent 20 is positioned proximal of the distal end of the push catheter 14.

FIG. 4A illustrates the push catheter 14 in a first or engaged position in which the drainage stent 20 is coupled to the push catheter 14. In the engaged position, the tab 160 may be positioned in the second portion 154 of the slot 150 such that longitudinal movement of the push catheter 14 relative to the drainage stent 20 will not decouple the drainage stent 20 from the push catheter 14. For instance, a portion of the tubular wall of the drainage stent 20 may be located proximal of the tab 160 such that if the push catheter 14 is pulled proximally, the tab 160 will contact the tubular wall of the drainage stent 20, preventing disengagement of the drainage stent 20.

As shown in FIG. 4B at arrow A, in order to decouple the drainage stent 20 from the push catheter 14, the push catheter 14 may be rotated relative to the drainage stent 20 to move the tab 160 along the second portion 154 to a location that intersects the first portion 152 of the slot 150. Once the tab 160 is located at the intersection of the first portion 152 and the second portion 154 of the slot 150, the push catheter 14 may be moved longitudinally relative to the drainage stent 20 in a proximal direction, shown by arrow B of FIG. 4B, to a second or disengaged position to withdraw the tab 160 from the slot 150. With the tab 160 decoupled from the slot 150, the push catheter 14 may be withdrawn while the drainage stent 20 is maintained at the target location in a body lumen.

FIGS. 5A-5D illustrate the functionality of a third exemplary locking structure for selectively coupling the drainage stent 20 to an elongate shaft of the drainage stent delivery system 10. Although the drainage stent 20 is illustrated as being selectively coupled to the push catheter 14 of the drainage stent delivery system 10, it is understood that in some embodiments the drainage stent 20 may be selectively coupled to the guide catheter 12, or another elongate shaft, in the manner described with regard to FIGS. 5A-5D.

In the embodiment shown in FIGS. 5A-5D, the push catheter 14 includes an inner tubular member 46 and an outer tubular member 44 slidably disposed over the inner tubular member 46. Thus, the outer tubular member 44 may be longitudinally actuatable or translatable relative to the inner tubular member 46, such as with an actuation mechanism proximate the handle assembly 16. Additionally or alternatively, in some embodiments the outer tubular member 44 and/or the inner tubular member 46 may be rotatable relative to one another (e.g., the outer tubular member 44 may be rotatable around the inner tubular member 46 and/or the inner tubular member 46 may be rotatable within the outer tubular member 44). When the drainage stent 20 is coupled to the push catheter 14, a distal portion of the inner tubular member 46 may extend into the lumen of the drainage stent 20 while the distal end 45 of the outer tubular member 44 may face and/or abut the proximal end 56 of the drainage stent 20.

Figure 5A:
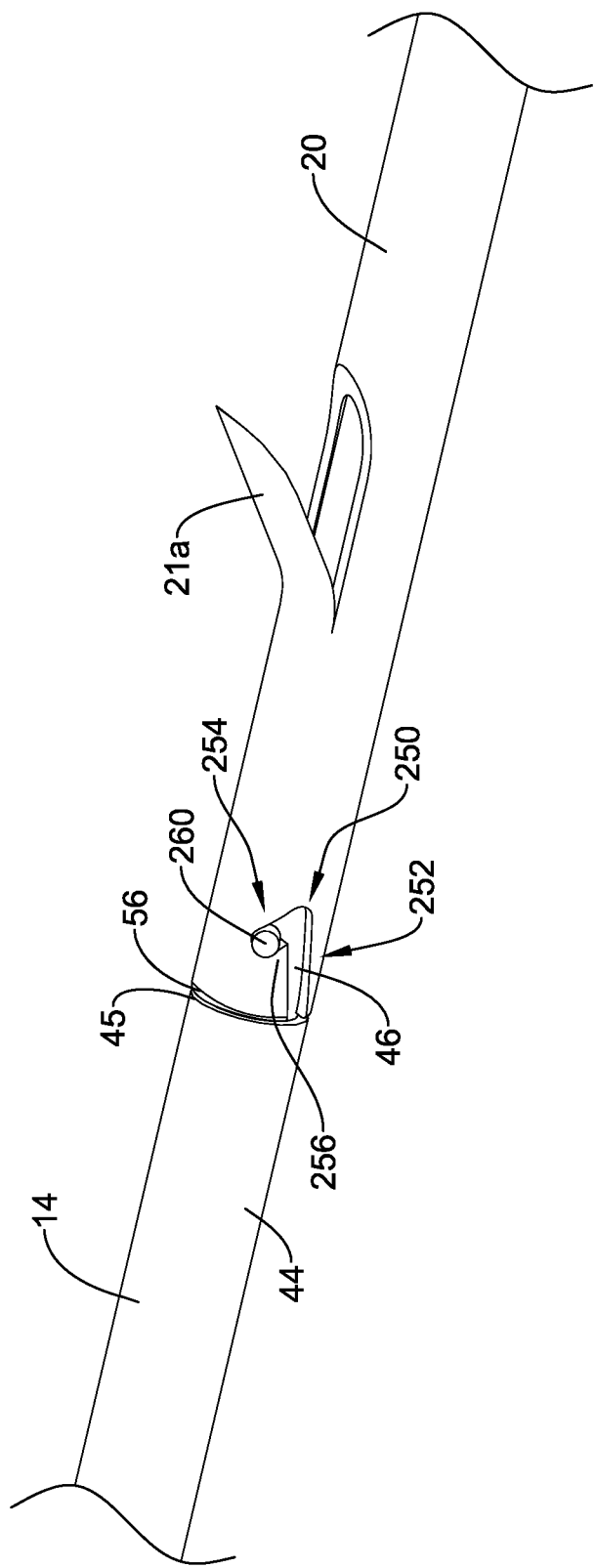

As shown in FIG. 5A, the drainage stent 20 may include an engaging feature which engages with an engaging feature of the push catheter 14 to selectively lock the drainage stent 20 to the push catheter 14. For instance, inner tubular member 46 of the push catheter 14 may include a tab 260, such as a radially extending protrusion, extending from the tubular wall of the inner tubular member 46 of the push catheter 14. The tab 260 may be configured to be inserted into an opening of the drainage stent 20, such as the slot 250. The slot 250 may be formed in or through the tubular wall of the drainage stent 20. As shown in FIGS. 5A-5D, in some instances, the slot 250 may be a V-shaped slot, opening out to the proximal end 56 of the drainage stent 20. The slot 250 may extend through the entire thickness of the tubular wall of the drainage stent 20, or the slot 250 may only extend through a portion of the thickness of the tubular wall of the drainage stent 20 (e.g., a groove).

The slot 250, shown as a V-shaped slot, may include a first portion 252 extending distally from the proximal end 56 of the drainage stent 20 and a second portion 254 extending from the first portion 252 in a direction deviating from the first portion 252. In some instances, the second portion 254 may extend proximally from the intersection point of the first portion 252 and the second portion 254. In some instances, the second portion 254 may be angled from the first portion 252 in the range of about 10° to about 45°, about 10° to about 60°, about 10° to about 90°, about 30° to about 60°, about 60° to about 90°, about 90°, less than 90°, or greater than 90°. The material remaining of the tubular wall of the drainage stent 20 between the first portion 252 and the second portion 254 of the slot 250 proximal of the intersection point of the first portion 252 and the second portion 254 of the slot 250 may provide a wedge 256 which extends distal of the proximalmost portion of the second portion 254 of the slot 250.

A distal portion of the inner tubular member 46 of the push catheter 14 may extend into the lumen of the drainage stent 20 such that the tab 260 engages with the slot 250 of the drainage stent 20. Thus, the outer diameter of the distal portion of the inner tubular member 46 of the push catheter 14 may be less than the inner diameter of the drainage stent 20, while the radial extent of the tab 260 may be greater than the inner diameter of the drainage stent 20. The distal portion of the inner tubular member 46 of the push catheter 14 may extend into and/or through the lumen of the drainage stent 20 for any desired length such that the proximal end 56 of the drainage stent 20 is positioned proximal of the distal end of the inner tubular member 46 of the push catheter 14. For instance, with the tab 260 engaged with the slot 250, the distal end of the inner tubular member 46 of the push catheter 14 may be positioned at or proximal of the proximal barb 21a, between the proximal barb 21a and the distal barb 21b, or at or distal of the distal barb 21b, in some embodiments.

FIG. 5A illustrates the push catheter 14 in a first or engaged position in which the drainage stent 20 is coupled to the push catheter 14. In the engaged position, the tab 260 may be positioned in the second portion 254 of the slot 250 with at least a portion of the tab 260 located proximal of the distalmost extent of the wedge 256 between the first portion 252 and the second portion 254. The distal end 45 of the outer tubular member 44 of the push catheter 14 may be located proximate the proximal end 56 of the drainage stent 20 such that the tab 260 is restricted from moving distally relative to the drainage stent 20 a sufficient distance to place the proximalmost extent of the tab 260 distal of the distalmost extent of the wedge 256. In some embodiments, the distal end 45 of the outer tubular member 44 may abut the proximal end 56 of the drainage stent 20. Thus, longitudinal and/or rotational movement of the push catheter 14 relative to the drainage stent 20 will not decouple the drainage stent 20 from the push catheter 14 in the first or engaged position since the tab 260 is prevented from moving into the first portion 252 of the slot 250 in the first or engaged position.

Figure 5B:
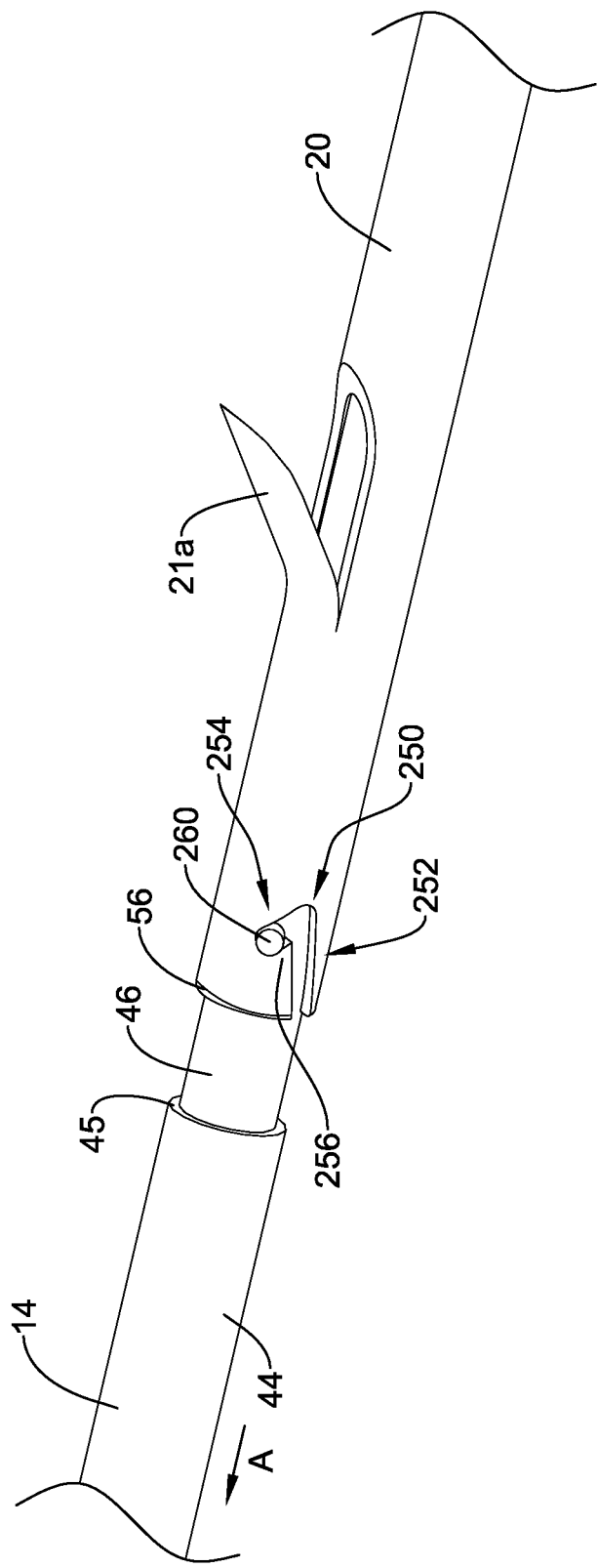
Figure 5D:
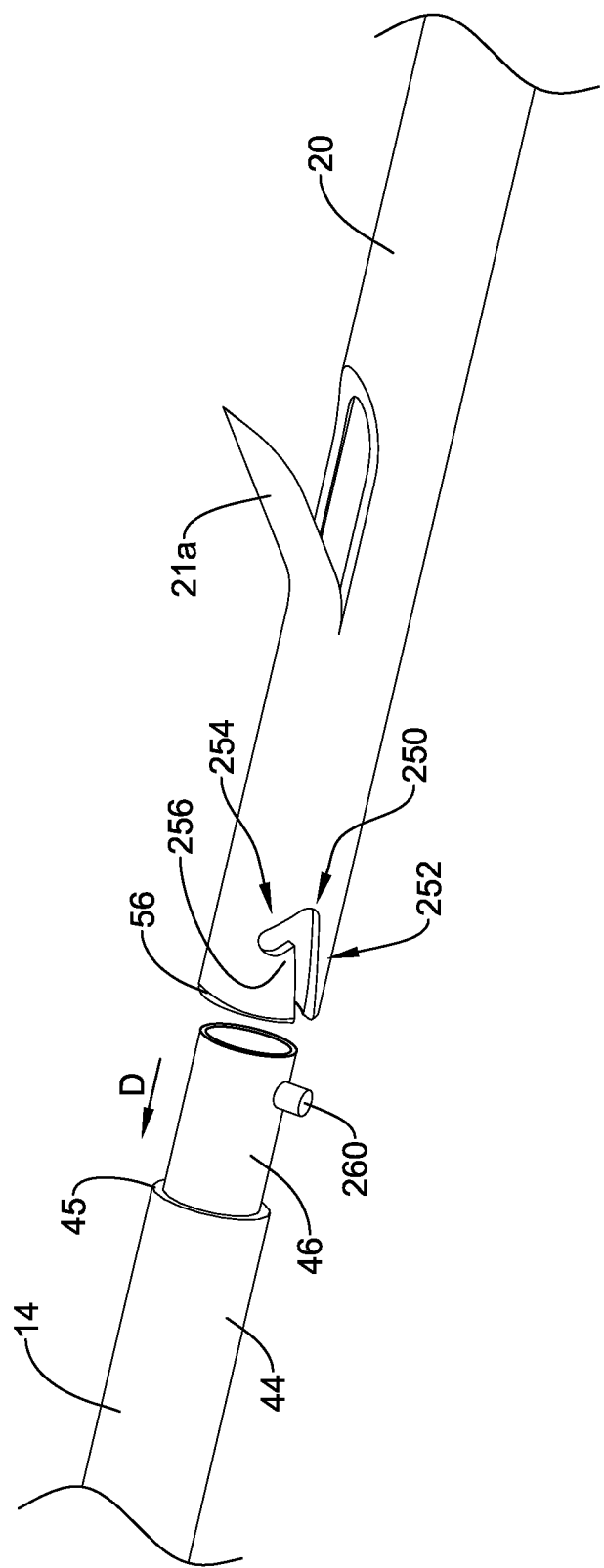

As shown in FIG. 5B at arrow A, in order to decouple the drainage stent 20 from the push catheter 14, initially the outer tubular member 44 of the push catheter 14 may be moved proximally relative to the drainage stent 20 a sufficient distance to allow the proximalmost extent of the tab 260 to move distal of the distalmost extent of the wedge 256. Concurrently or subsequent to moving the distal end 45 of the outer tubular member 44 away from the proximal end 56 of the drainage stent 20, the inner tubular member 46 of the push catheter 14 may be moved distally (shown at arrow B of FIG. 5C) and rotated (shown at arrow C of FIG. 5C) relative to the drainage stent 20 to move the tab 260 along the second portion 254 to a location that intersects the first portion 252 of the slot 250. When the tab 260 is located at the intersection point of the first portion 252 and the second portion 254 of the slot 250, the proximalmost extent of the tab 260 may be positioned distal of the distalmost extent of the wedge 256, allowing the tab 260 to move into the first portion 252. Once the tab 260 is located at the intersection of the first portion 252 and the second portion 254 of the slot 250, the push catheter 14 may be moved longitudinally relative to the drainage stent 20 in a proximal direction (shown at arrow D of FIG. 5D), thus moving the tab 260 proximally through the first portion 252 of the slot 250, to a second or disengaged position to withdraw the tab 260 from the slot 250. With the tab 260 decoupled from the slot 250, the push catheter 14 may be withdrawn while the drainage stent 20 is maintained at the target location in a body lumen.

Figure 6B:
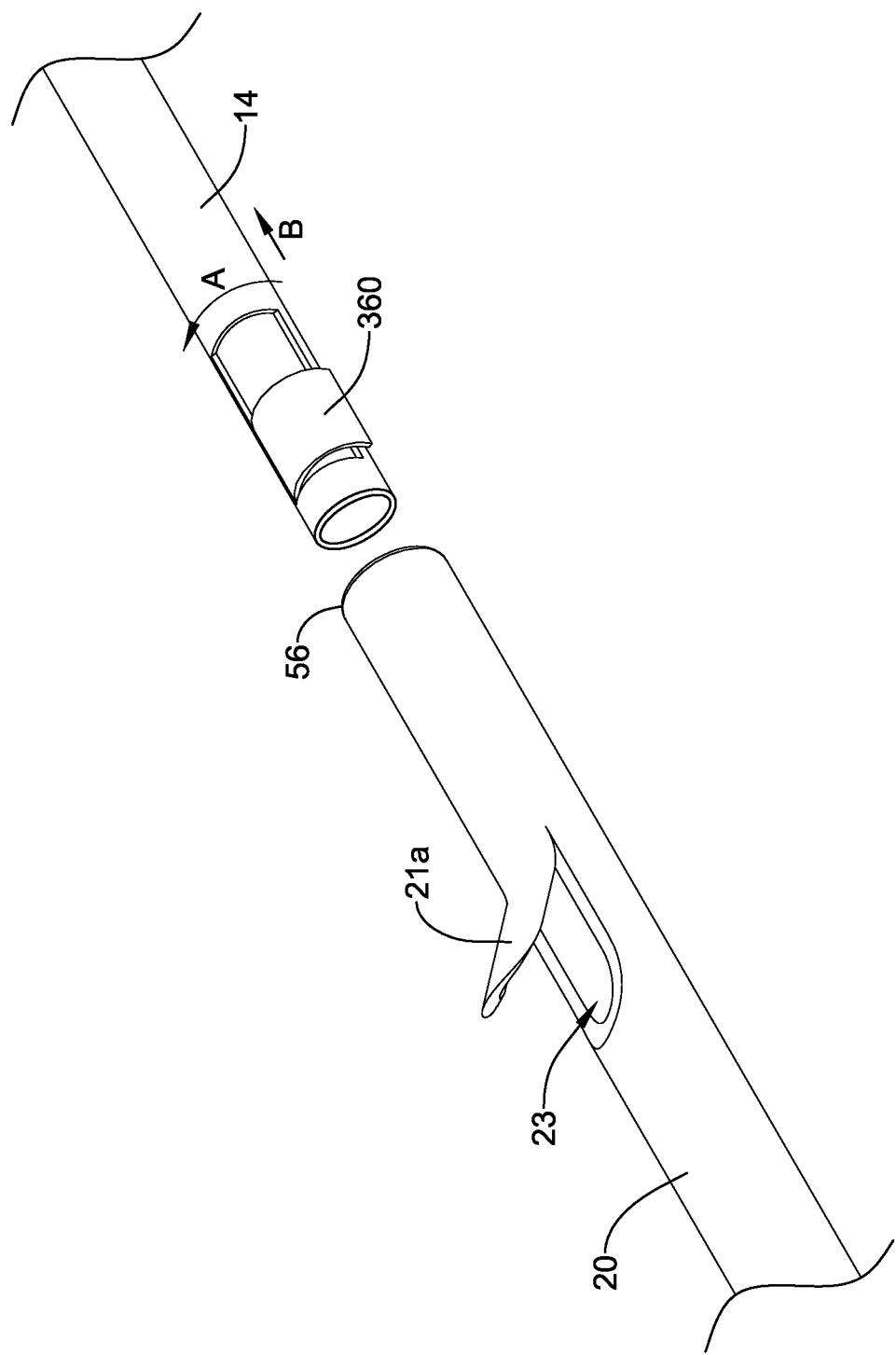

FIGS. 6A and 6B illustrate the functionality of a fourth exemplary locking structure for selectively coupling the drainage stent 20 to an elongate shaft of the drainage stent delivery system 10. Although the drainage stent 20 is illustrated as being selectively coupled to the push catheter 14 of the drainage stent delivery system 10, it is understood that in some embodiments the drainage stent 20 may be selectively coupled to the guide catheter 12, or another elongate shaft, in the manner described with regard to FIGS. 6A and 6B.

As shown in FIG. 6A, the drainage stent 20 may include an engaging feature which engages with an engaging feature of the push catheter 14 to selectively lock the drainage stent 20 to the push catheter 14. For instance, the push catheter 14 may include a tab 360, such as an arcuate flap, extending in a circumferential direction relative to the central longitudinal axis of the push catheter 14 from the tubular wall of the push catheter 14. The tab 360 may be cut or otherwise formed from a portion of the tubular wall of the push catheter 14, or the tab 360 may be a separate piece attached to the tubular wall of the push catheter 14. The tab 360 may be configured to be inserted into an opening of the drainage stent 20, such as the opening 23 formed consequent the barb 21a being cut from the tubular wall of the drainage stent 20. The opening 23 proximate the barb 21a may be formed in or through the tubular wall of the drainage stent 20.

A distal portion of the push catheter 14, from which the tab 360 extends from, may extend into the lumen of the drainage stent 20 such that the tab 360 extends outward through the opening 23 of the drainage stent 20. Thus, the outer diameter of the distal portion of the push catheter 14 may be less than the inner diameter of the drainage stent 20, while the radial extent of the tab 360 may be greater than the inner diameter of the drainage stent 20, extending into or through the opening 23. The distal portion of the push catheter 14 may extend into and/or through the lumen of the drainage stent 20 for any desired length such that the proximal end 56 of the drainage stent 20 is positioned proximal of the distal end of the push catheter 14. For instance, with the tab 360 engaged with the opening 23, the distal end of the push catheter 14 may be positioned proximate the proximal barb 21a, between the proximal barb 21a and the distal barb 21b, or at or distal of the distal barb 21b, in some embodiments.

Figure 6C:
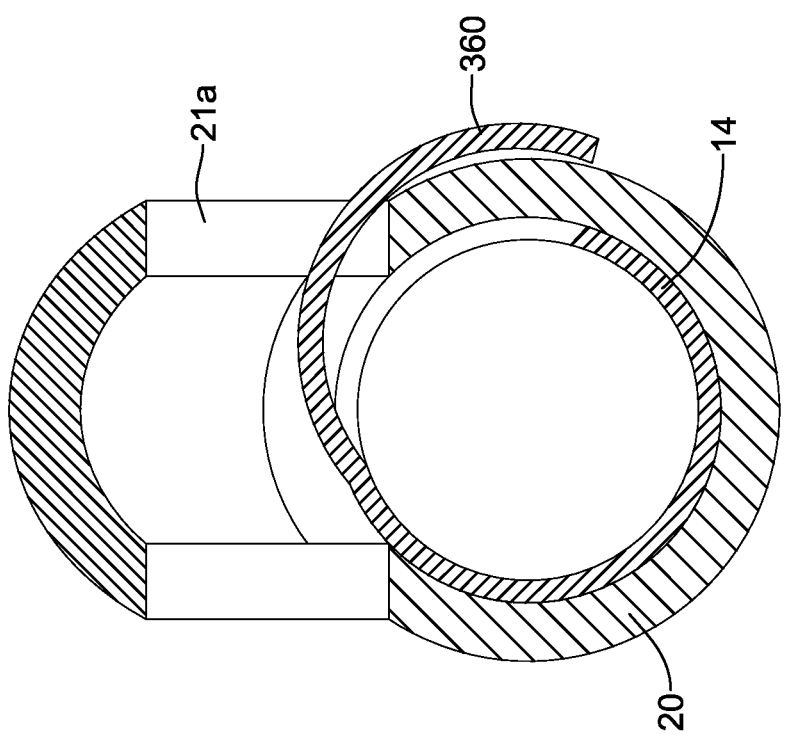
FIG. 6C is a transverse cross-sectional view of the engaged locking structure shown in FIG. 6A taken along line 6C-6C.

FIG. 6A illustrates the push catheter 14 in a first or engaged position in which the drainage stent 20 is coupled to the push catheter 14. In the engaged position, the tab 360 may extend outward into or through the opening 23 proximate the proximal barb 21a of the drainage stent 20 while the distal portion of the push catheter 14 is located in the lumen of the drainage stent 20. In some instances, as shown in FIG. 6C, which is a cross-sectional view taken along line 6C-6C of FIG. 6A, the tab 360 may extend outward through the opening 23 and wrap around a portion of the exterior of the drainage stent 20. The tab 360 may be positioned through the opening 23 such that longitudinal movement of the push catheter 14 relative to the drainage stent 20 will not decouple the drainage stent 20 from the push catheter 14. For instance, a portion of the tubular wall of the drainage stent 20 may be located proximal of the tab 360 such that if the push catheter 14 is pulled proximally, the tab 360 will contact the tubular wall of the drainage stent 20, preventing disengagement of the drainage stent 20.

As shown in FIG. 6B at arrow A, in order to decouple the drainage stent 20 from the push catheter 14, the push catheter 14 may be rotated relative to the drainage stent 20 to move the tab 360 into the lumen of the drainage stent 20. As the push catheter 14 is rotated, the tab 360 may deflect radially inward toward the central longitudinal axis of the push catheter 14 to a position in which the tab 360 is located radially inward of the tubular wall of the drainage stent 20. Once the tab 360 is rotated into the lumen of the drainage stent 20, the push catheter 14 may be moved longitudinally relative to the drainage stent 20 in a proximal direction, shown by arrow B of FIG. 6B, to a second or disengaged position to withdraw the tab 360 proximally from the opening 23. With the tab 360 decoupled from the opening 23, the push catheter 14 may be withdrawn while the drainage stent 20 is maintained at the target location in a body lumen.

Figure 7A:
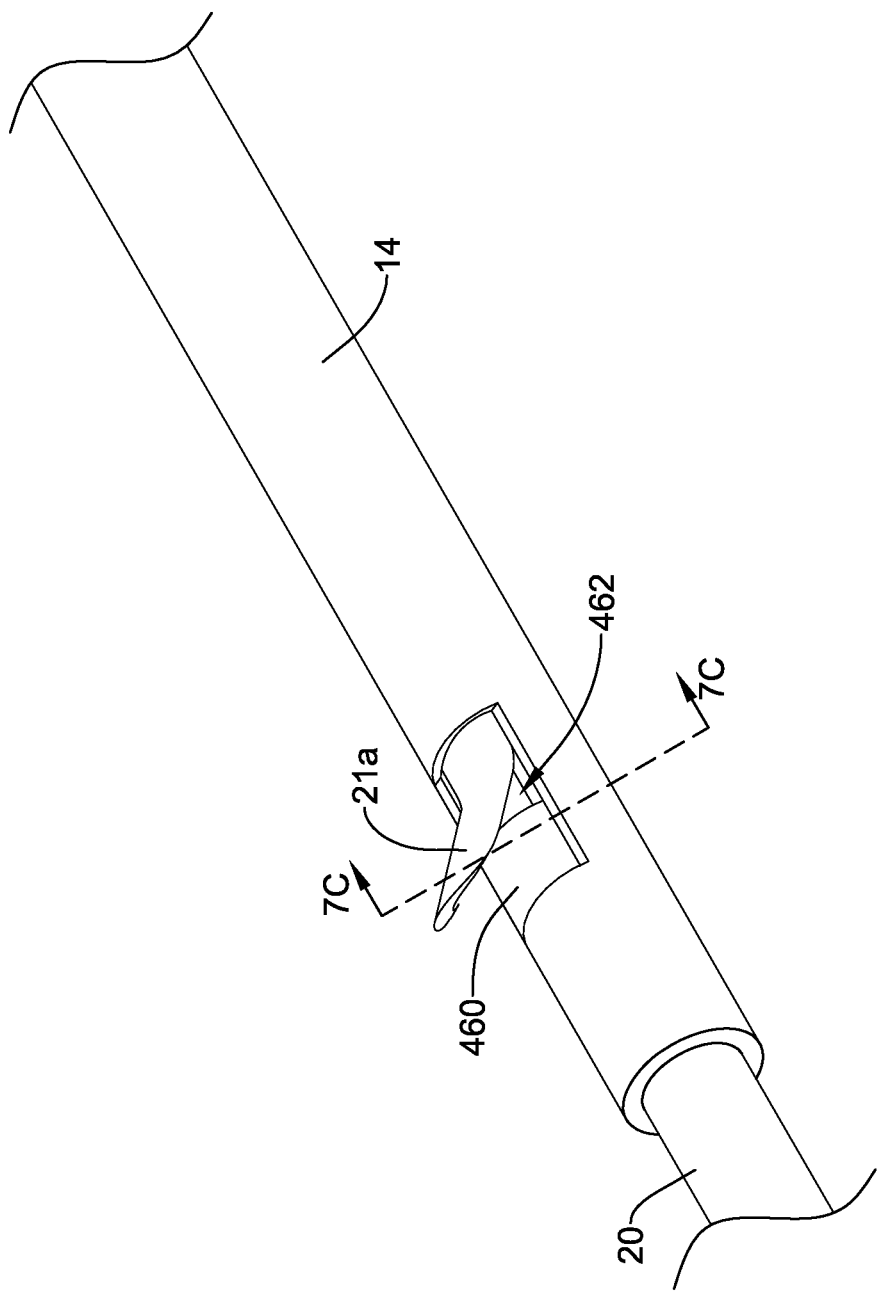
FIGS. 7A and 7B are perspective views illustrating the functionality of yet another locking structure for selectively coupling a stent to an elongate shaft of a delivery system.
Figure 7B:
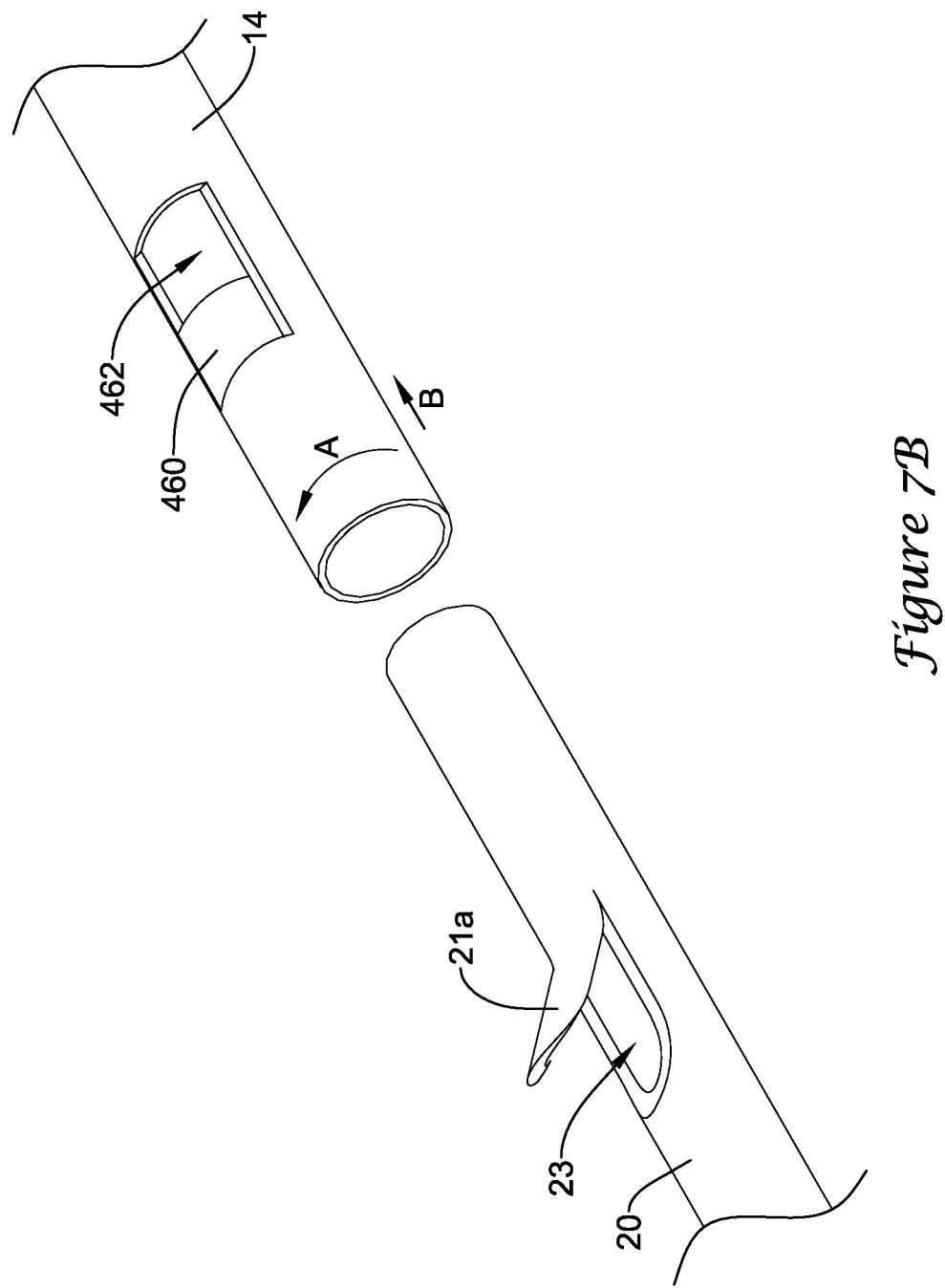

FIGS. 7A and 7B illustrate the functionality of a fifth exemplary locking structure for selectively coupling the drainage stent 20 to an elongate shaft of the drainage stent delivery system 10. Although the drainage stent 20 is illustrated as being selectively coupled to the push catheter 14 of the drainage stent delivery system 10, it is understood that in some embodiments the drainage stent 20 may be selectively coupled to the guide catheter 12, or another elongate shaft, in the manner described with regard to FIGS. 7A and 7B.

As shown in FIG. 7A, the drainage stent 20 may include an engaging feature which engages with an engaging feature of the push catheter 14 to selectively lock the drainage stent 20 to the push catheter 14. For instance, the push catheter 14 may include a tab 460, such as an arcuate flap, extending in a circumferential direction relative to the central longitudinal axis of the push catheter 14 from the tubular wall of the push catheter 14. The tab 460 may be cut or otherwise formed from a portion of the tubular wall of the push catheter 14, or the tab 460 may be a separate piece attached to the tubular wall of the push catheter 14. The tab 460 may be configured to be inserted into an opening of the drainage stent 20, such as the opening 23 formed consequent the barb 21a being cut from the tubular wall of the drainage stent 20. The opening 23 proximate the barb 21a may be formed in or through the tubular wall of the drainage stent 20.

A distal portion of the push catheter 14, from which the tab 460 extends from, may extend over the drainage stent 20 such that the tab 460 extends outward through the opening 23 of the drainage stent 20. Thus, the inner diameter of the distal portion of the push catheter 14 may be greater than the outer diameter of the drainage stent 20, while the radial extent of the tab 460 may be less than the outer diameter of the drainage stent 20, extending into or through the opening 23. The distal portion of the push catheter 14 may extend over the drainage stent 20 for any desired length such that the proximal end 56 of the drainage stent 20 is positioned proximal of the distal end of the push catheter 14. For instance, with the tab 460 engaged with the opening 23, the distal end of the push catheter 14 may be positioned proximate the proximal barb 21a, between the proximal barb 21a and the distal barb 21b, or at or distal of the distal barb 21b, in some embodiments.

Figure 7C:
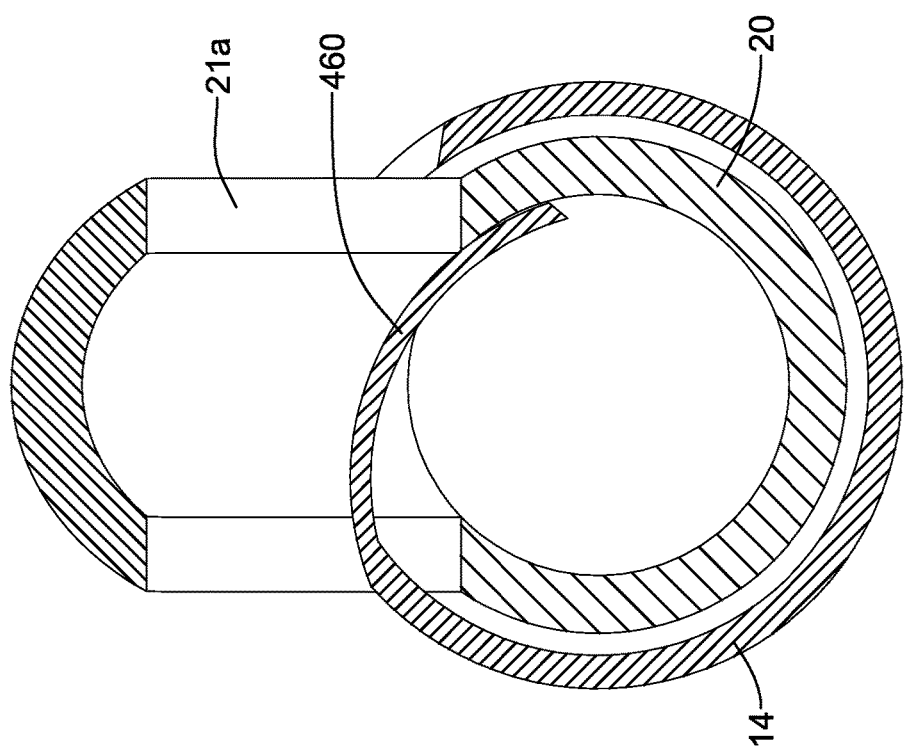
FIG. 7C is a transverse cross-sectional view of the engaged locking structure shown in FIG. 7A taken along line 7C-7C.

FIG. 7A illustrates the push catheter 14 in a first or engaged position in which the drainage stent 20 is coupled to the push catheter 14. In the engaged position, the tab 460 may extend inward into or through the opening 23 proximate the proximal barb 21a of the drainage stent 20 while the distal portion of the push catheter 14 is located circumferentially around the drainage stent 20. In some instances, as shown in FIG. 7C, which is a cross-sectional view taken along line 7C-7C of FIG. 7A, the tab 460 may extend inward through the opening 23 and into the lumen of the drainage stent 20. The tab 460 may be positioned through the opening 23 such that longitudinal movement of the push catheter 14 relative to the drainage stent 20 will not decouple the drainage stent 20 from the push catheter 14. For instance, a portion of the tubular wall of the drainage stent 20 may be located proximal of the tab 460 such that if the push catheter 14 is pulled proximally, the tab 460 will contact the tubular wall of the drainage stent 20, preventing disengagement of the drainage stent 20. Furthermore, in the first or engaged position, the barb 21a of the drainage stent 20 may extend outward through an opening 462 formed in the tubular wall of the push catheter 14 proximal of the tab 460. Thus, interaction of the tab 460 and the barb 21a may prevent disengagement of the drainage stent 20 from the push catheter 14.

As shown in FIG. 7B at arrow A, in order to decouple the drainage stent 20 from the push catheter 14, the push catheter 14 may be rotated relative to the drainage stent 20 to move the tab 460 out of the opening 23 and lumen of the drainage stent 20. As the push catheter 14 is rotated, the tab 460 may deflect radially outward away from the central longitudinal axis of the push catheter 14 to a position in which the tab 460 is located radially outward of the tubular wall of the drainage stent 20. Furthermore, as the push catheter 14 is rotated, the barb 21a of the drainage stent 20 may deflect radially inward into the lumen of the push catheter 14 to a position in which the barb 21a is located radially inward of the inner diameter of the push catheter 14. Once the tab 460 is rotated out of the opening 23 and lumen of the drainage stent 20 and the barb 21a is deflected into the lumen of the push catheter 14, the push catheter 14 may be moved longitudinally relative to the drainage stent 20 in a proximal direction, shown by arrow B of FIG. 7B, to a second or disengaged position to withdraw the tab 460 proximally from the opening 23 and the barb 21a. With the tab 460 decoupled from the opening 23 and the barb 21a deflected inward into the lumen of the push catheter 14, the push catheter 14 may be withdrawn while the drainage stent 20 is maintained at the target location in a body lumen.

In some embodiments, the slot 50, 150, 250 may only extend through a portion of the thickness of the tubular wall of the drainage stent 20, thus defining a groove in the tubular wall of the drainage stent 20. The tab 60, 160, 260 could be configured to engage in this groove, which would be located in a surface of the drainage stent 20. In some embodiments, the tab 60, 160, 260 and slot 50, 150, 250 (which may be a groove in some instances) may be designed to form an interference fit, permitting further control of the drainage stent 20 prior to deployment of the drainage stent 20. For example, in some embodiments the tab 60, 160, 260 and the slot 50, 150, 250 may fit together as a wedge or by elastic deformation of one or both of the engaging features.

Furthermore, in some instances the orientation of the engaging feature of the push catheter 14 and/or the engaging feature of the drainage stent 20 may be altered. For example, instead of extending radially outward as shown in FIGS. 3A-3B, 4A-4B and 5A-5D, the tab 60, 160, 260 could extend radially inward into or through the slot 50, 150, 250 (which may be a groove on the outer surface of the drainage stent 20 in some instances) from an outer surface of the drainage stent 20.

In some embodiments, one or more of the engaging features may extend beyond the functional length of the push catheter 14 and/or the drainage stent 20. For example, referring to FIG. 4B, the slot 150 could be located on a tab (not shown) extending from the proximal end 56 of the drainage stent 20.

It is noted that although several examples of an engaging feature of the drainage stent 20 which engages with an engaging feature of the push catheter 14 to selectively lock the drainage stent 20 to the push catheter 14 are illustrated herein, in other embodiments the engaging feature of the drainage stent 20 and the engaging feature of the push catheter 14 may be reversed, such that the push catheter 14 includes an opening or other engaging feature that receives the tab or other engaging feature of the drainage stent 20.

In some instances, the delivery system 10 may be configured such that the guide catheter 12 may lock the engaging features of locking structures in place. Once the guide catheter 12 is withdrawn proximally beyond the engaging features, the engaging features may be unlocked from one another to release the drainage stent 20. For example, the guide catheter 12 may be used to push a tab radially outward into engagement with a slot or hole to lock the drainage stent 20 to the delivery system 10. As the guide catheter 12 is withdrawn, the tab may be disengaged from the slot or hole, unlocking the drainage stent 20 from the delivery system 10. In such an instance, relative rotational movement between the drainage stent 20 and a component of the delivery system 10 may be unnecessary.

Although several illustrated embodiments of the disclosed stent locking structures are illustrated as being incorporated into a delivery system for delivering a drainage stent, it is understood that the stent locking structures may also be used to selectively lock other stent or endoprosthesis devices to a delivery system. For example, in some instances the stent locking structures described herein may be used to selectively lock a vascular stent to an elongate member of a delivery system for delivering the vascular stent to a target location within the vasculature of a patient.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A stent delivery system comprising:
an elongate shaft of a medical device, the elongate shaft having a proximal end, a distal end, and a lumen extending therebetween;
a stent having a proximal end and a distal end, the stent including an outwardly extending barb and an opening extending through a sidewall of the stent proximate the barb, the stent being selectively coupled to a distal portion of the elongate shaft such that the proximal end of the stent is positioned proximal of the distal end of the elongate shaft; and
a locking mechanism for selectively coupling the stent to the elongate shaft, the locking mechanism including a tab fixed to and extending from the elongate shaft through the opening of the stent, wherein the tab is removable from the opening through rotational movement of the tab via rotational motion of the elongate shaft relative to the stent.

2. The stent delivery system of claim 1, wherein the tab extends outward through the opening with a free end of the tab located radially outward of the sidewall of the stent.

3. The stent delivery system of claim 1, wherein the tab extends inward through the opening with a free end of the tab located radially inward of the sidewall of the stent.

4. The stent delivery system of claim 1, wherein the distal portion of the elongate shaft extends into the stent.

5. The stent delivery system of claim 1, wherein the distal portion of the elongate shaft surrounds a proximal portion of the stent.

6. The stent delivery system of claim 1, wherein the tab is a monolithic portion of the elongate shaft.

7. The stent delivery system of claim 1, wherein the tab is an arcuate flap.

8. The stent delivery system of claim 1, wherein the barb is located intermediate the proximal and distal ends of the stent.

9. The stent delivery system of claim 1, wherein the tab extends circumferentially from the elongate shaft.

10. A stent delivery system comprising:
an elongate shaft of a medical device, the elongate shaft having a proximal end, a distal end, a lumen extending therebetween, and a longitudinal axis;
a stent including a tubular member having a proximal end and a distal end, the stent including an outwardly extending barb and an opening proximate the barb extending through the tubular member from an inner surface of the tubular member to an outer surface of the tubular member, the stent being selectively coupled to a distal portion of the elongate shaft such that the proximal end of the stent is positioned proximal of the distal end of the elongate shaft; and
a locking mechanism for selectively coupling the stent to the elongate shaft, the locking mechanism including a tab fixed to and extending from the elongate shaft through the opening of the stent;
wherein the tab is removable from the opening through rotational movement of the tab via rotational motion of the elongate shaft relative to the stent about the longitudinal axis of the elongate shaft.

11. The stent delivery system of claim 10, wherein the elongate shaft includes an inner tubular member and an outer tubular member disposed about the inner tubular member.

12. The stent delivery system of claim 11, wherein the outer tubular member is longitudinally actuatable relative to the inner tubular member.

13. The stent delivery system of claim 12, wherein the tab extends from a distal portion of the inner tubular member.

14. The stent delivery system of claim 13, wherein the distal portion of the inner tubular member extends into the stent.

15. The stent delivery system of claim 14, wherein the tab extends outward beyond the outer surface of the stent.

16. The stent delivery system of claim 12, wherein the tab extends from a distal portion of the outer tubular member.

17. The stent delivery system of claim 16, wherein the distal portion of the outer tubular member surrounds a proximal portion of the stent.

18. The stent delivery system of claim 10, wherein the tab is an arcuate flap.

19. The stent delivery system of claim 10, wherein the tab is a monolithic portion of the elongate shaft.

20. The stent delivery system of claim 10, wherein the tab extends perpendicular to the longitudinal axis of the elongate shaft.

* * * * *